United States Patent [19]

Cognacq et al.

[11] 4,109,008
[45] Aug. 22, 1978

[54] HYDRAZINE DERIVATIVES USEFUL AS ANTI-HYPERTENSIVES

[75] Inventors: Jean-Calude Cognacq, Garches; Bernard Schweisguth, Meudon; Jean-Marie Teulon, La Celle Saint-Cloud, all of France

[73] Assignee: Hexachimie, Rueil-Malmaison, France

[21] Appl. No.: 755,194

[22] Filed: Dec. 29, 1976

[30] Foreign Application Priority Data

Jan. 7, 1976 [GB] United Kingdom ............ 562/76

[51] Int. Cl.² .............. C07D 235/26; C07D 403/12; A61K 31/415
[52] U.S. Cl. .............. 424/273 R; 260/294.8 G; 260/296 R; 260/564 F; 542/419; 548/305
[58] Field of Search .............. 548/305; 542/419; 260/294.8 C, 295.5 B; 424/273 R

[56] References Cited

U.S. PATENT DOCUMENTS

| Re. 29,358 | 8/1977 | Tomcufcik | 542/419 |
|---|---|---|---|
| 4,005,068 | 1/1977 | Hunger et al. | 548/305 |
| 4,012,371 | 3/1977 | Roueche et al. | 548/305 |
| 4,024,125 | 5/1977 | Kunstmann et al. | 548/305 |

OTHER PUBLICATIONS

El'tsov, I, Chem. Abst., 1963, vol. 58, cols. 4539–4540.
El'tsov, II, Chem. Abst., 1963, vol. 59, cols. 11471–11472.

Primary Examiner—Natalie Trousof

[57] ABSTRACT

The invention provides novel hydrazine derivatives of the formula:

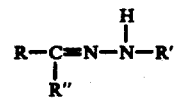

in which R is a variously substituted oxy or thio substituted phenyl radical, 2-oxobenzimidazol-5-yl radical or 3-pyridyl radical;

R' is a radical of formula:

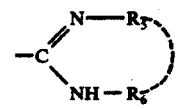

in which $R_5$ and $R_6$ taken separately are each hydrogen, and taken together form, with the nitrogen atoms to which they are attached, an imidazolinyl radical of formula;

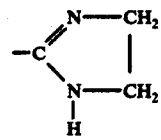

and R" is hydrogen or lower alkyl, and the pharmaceutically acceptable addition salts, with non-toxic acids, of these hydrazine derivatives.

These compounds are useful as anti-hypertensive agents.

8 Claims, No Drawings

HYDRAZINE DERIVATIVES USEFUL AS ANTI-HYPERTENSIVES

The present invention provides, as new compounds, the hydrazine derivatives of the formula:

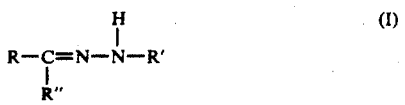

in which R is either (a) a substituted phenyl radical of formula:

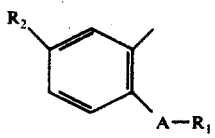

wherein A is O, S, or a direct bond, $R_1$ is lower alkyl, lower alkenyl, lower alkynyl, benzyl, or cyclopropyl (by "lower" is meant of up to 4 carbon atoms) and $R_2$ is hydrogen or halogen, or (b) the radical of formula:

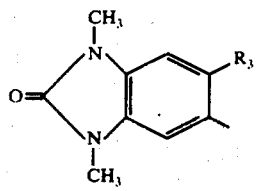

wherein $R_3$ is hydrogen, methyl or methoxy, or (c) a radical of formula:

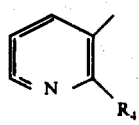

wherein $R_4$ is halogen, alkylthio or benzylthio; R' is a radical of formula:

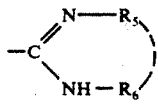

in which $R_5$ and $R_6$ taken separately are each hydrogen, and taken together form, with the nitrogen atoms to which they are attached, an imidazolinyl radical of formula:

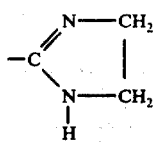

and R" is hydrogen or lower alkyl, and the pharmaceutically acceptable addition salts, with non-toxic acids, of these hydrazine derivatives.

The invention also provides a process for the preparation of the compounds of formula (I), which comprises reacting an aldehyde or ketone of the formula R—CO—R" (R and R" having the meanings given above) with a salt of a hydrazine derivative of formula: $H_2N$—NH—R', wherein R' is as defined above, especially aminoguanidine sulphate or with hydrazinoimidazoline hydrobromide in an organic polar solvent, preferably a lower alcohol solvent, especially methanol or ethanol, or a glycol, optionally diluted with water, preferably at the reflux temperature of the solvent.

The compounds of formula (I) and their salts possess pharmacological properties which make them of value in therapy. In particular, they are active on the cardiovascular system, especially as hypotensive agents.

The invention thus includes within its scope pharmaceutical compositions comprising a compound of formula I or a non-toxic acid addition salt thereof in association with a pharmaceutical carrier, e.g. in the form of a tablet, pill, capsule, powder, syrup, elixir, or sterile injectable solution or suspension.

The invention is illustrated in the following Examples.

EXAMPLE 1

N-[o-(Prop-2-Ynoxy)-Benzylidene]-N'-Amidino-Hydrazine

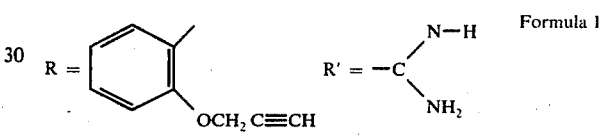

A mixture of 0.1 mol of o-(prop-2-ynoxy)-benzaldehyde, 0.05 mol of neutral aminoguanidine sulphate and 200 cm³ of ethanol is heated under reflux for 6 hours.

The solvent is evaporated in vacuo, the residue is taken up in 300 cm³ of water, the solution is rendered alkaline with concentrated ammonia and extracted with ether, the ether extract is dried over sodium sulphate and the solvent is then evaporated in vacuo.

The corresponding maleate salt is prepared as follows: the residue is dissolved in 150 cm³ of ethyl acetate and mixed with a solution of 0.1 mol of maleic acid in 100 cm³ of ethyl acetate, the mixture is left to stand for 2 hours and is filtered, and the filter residue is washed with ethyl acetate and dried to give 24 g of N-[o-(prop-2-ynoxy)-benzylidene]-N'-amidino-hydrazine maleate.

Melting point = 157° C.

EXAMPLE 2

N-[o-(Prop-2-Enoxy)-Benzylidene]-N'-Amidino-Hydrazine

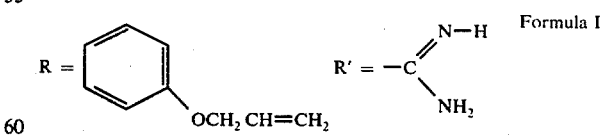

The procedure of Example 1 is repeated, but using 0.1 mol of o-(prop-2-enoxy)-benzaldehyde in place of o-(prop-2-ynoxy)-benzaldehyde.

After evaporation of the ether, the base is recrystallised from a 70/30 mixture of isopropanol/petroleum ether to give 16 g of N-[o-(prop-2-enoxy)-benzylidene]-N'-amidino-hydrazine.

Melting point = 124° C.

EXAMPLE 3

N-[o-(Prop-2-Enethio)-Benzylidene]-N'-Amidino-Hydrazine

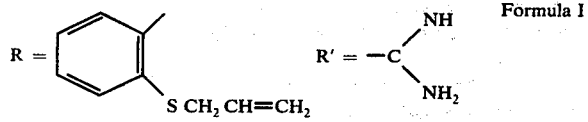

Formula I

The procedure of Example 1 is repeated, but using 0.1 mol of o-(prop-2-enethio)-benzaldehyde in place of o-(prop-2-ynoxy)-benzaldehyde.

Finally, 26 g of N-[o-(prop-2-enethio)-benzylidene]-N'-amidino-hydrazine maleate are obtained.

Melting point = 145° C.

EXAMPLE 4

N-[o-(Prop-2-Ynoxy)-Benzylidene]-N'-Imidazolino-Hydrazine

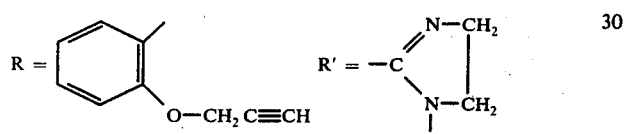

Formula I

A mixture of 0.1 mol of o-(prop-2-ynoxy)-benzaldehyde, 0.1 mol of hydrazino-imidazoline hydrobromide and 200 cm$^3$ of ethanol is heated under reflux for 6 hours.

It is allowed to return to ambient temperature and the product obtained is filtered off, washed with 50 cm$^3$ of ethanol and dried, to give 29 g of N-[o-(prop-2-ynoxy)-benzylidene]-N'-imidazolino-hydrazine hydrobromide.

Melting point = 231° C

EXAMPLE 5

N-[o-(Prop-2-Enoxy)-Benzylidene]-N'-Imidazolino-Hydrazine Hydrobromide

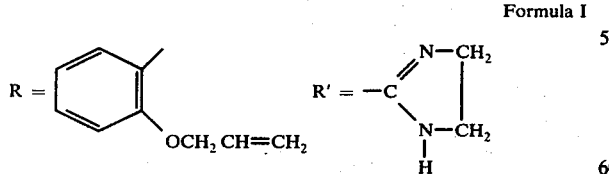

Formula I

The procedure of Example 4 is repeated, but using 0.1 mol of o-(prop-2-enoxy)-benzaldehyde in place of o-(prop-2-ynoxy)-benzaldehyde, to give 26 g of N-[o-(prop-2-enoxy)-benzylidene]-N'-imidazolino-hydrazine hydrobromide.

Melting point = 172° C.

EXAMPLE 6

N-[o-(Prop-2-Enethio)-Benzylidene]-N'-Imidazolino-Hydrazine Hydrobromide

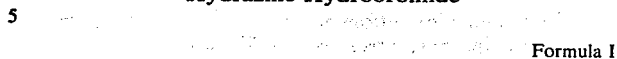
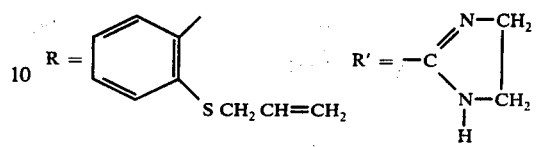

Formula I

The procedure of Example 4 is repeated, but using 0.1 mol of o-(prop-2-enethio)-benzaldehyde in place of o-(prop-2-ynoxy)-benzaldehyde, to give 25 g of N-[o-(prop-2-enethio)-benzylidene]-N'-imidazolino-hydrazine hydrobromide.

Melting point = 187° C.

EXAMPLE 7

N-(2-Methylthio-3-Pyridylidene)-N'-Imidazolino-Hydrazine Hydrobromide

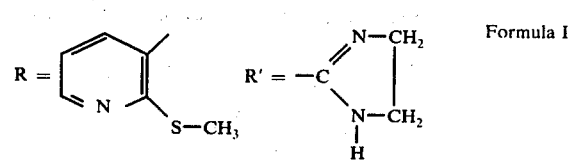

Formula I

A mixture of 13.4 g of 2-methylthio-nicotinaldehyde and 15.8 g of hydrazino-imidazoline hydrobromide in 160 cm$^3$ of ethanol and 100 cm$^3$ of water is heated under reflux for 7 hours.

The mixture is then concentrated in vacuo and the residue obtained is recrystallised from ethanol. 15.5 g of N-(2-methylthio-3-pyridylidene)-N'-imidazolino-hydrazine hydrobromide are thus obtained in the form of white crystals.

Melting point = 250°–251° C.

EXAMPLE 8

N-(2-Benzylthio-3-Pyridylidene)-N'-Amidino-Hydrazine Dihydrochloride

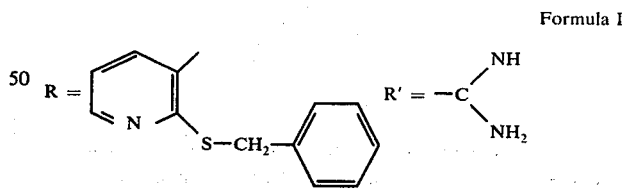

Formula I

A mixture of 15 g of 2-benzylthio-nicotinaldehyde and 8.7 g of neutral aminoguanidine sulphate in 120 cm$^3$ of ethanol and 120 cm$^3$ of water is heated under reflux for 12 hours.

The reaction mixture is then cooled, mixed with ice and rendered alkaline with concentrated ammonia.

The organic products are extracted with chloroform and the extract is washed with water and dried over sodium sulphate.

The residue obtained after evaporation of the chloroform in vacuo is taken up in a mixture of methanol and ether; a solution of hydrogen chloride in ether is added thereto, in the cold. The precipitate obtained is filtered off, washed with ether and then recrystallised from methanol. 12 g of N-(2-benzylthio-3-pyridylidene)-N'-amidino-hydrazine hydrochloride are thus obtained in the form of white crystals.

Melting point = 182°-6° C.

EXAMPLE 9

N-(o-Cyclopropylbenzylidene-N'-Amidino-Hydrazine

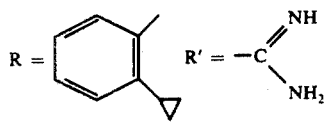

Formula I

A mixture of 0.1 mol of o-cyclopropylbenzaldehyde, 0.05 mol of neutral aminoguanidine sulphate and 200 cm³ of ethanol is heated under reflux for 6 hours.

A mixture is taken up in 400 cm³ of water and rendered alkaline with concentrated ammonia, stirred for one hour and then filtered, and the filter residue is washed with water until the pH is neutral, and is dried.

After recrystalliation from ether, 17 g of N-(o-cyclopropylbenzylidene)-N'-amidino-hydrazine are obtained.

Melting point = 139° C.

The corresponding maleate is prepared as follows: 0.05 mol of base is dissolved in 100 cm³ of ethyl acetate, and the solution thus obtained is added to a solution of 0.05 mol of maleic acid in 100 cm³ of ethyl acetate; the mixture is left to stand for 4 hours and is filtered; and the filter residue is washed with 50 cm³ of ethyl acetate and dried to give 15.4 g of N-(o-cyclopropylbenzylidene)-N'-amidino-hydrazine maleate.

Melting point = 170° C.

EXAMPLE 10

N-[2-(Prop-2'-Ynoxy)-5-Bromo-Benzylidene]-N'-Amidino-Hydrazine

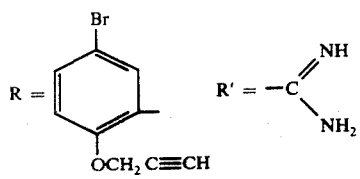

Formula I

A mixture of 0.1 mol of 2-(prop-2'-ynoxy)-5-bromo-benzaldehyde, 0.05 mol of neutral aminoguanidine sulphate and 200 cm³ of ethanol is heated under reflux for 6 hours.

The mixture is taken up in 400 cm³ of water, rendered alkaline with ammonia, stirred for one hour and the filtered, and the filter residue is washed with water until the pH is neutral, and is dried.

After recrystallisation from toluene, 25 g of N-[2-(prop-2'-ynoxy)-5-bromo-benzylidene]-N'-amidinohydrazine are obtained.

Melting point = 153° C.

EXAMPLE 11

N-(1,3-Dimethyl-2-Oxo-5-Benzimidazolylidene)-N'-Amidino-Hydrazine

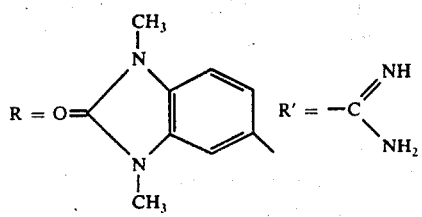

Formula I 15.5 g (0.08 mol) of 5-carboxaldehyde-1,3-dimethyl-benzimidazolone and 10.7 (0.04 mol) of amidino-hydrazine sulphate are added to 300 cm³ of 50% strength ethanol and this mixture is then heated under reflux for 13 hours, after which it is evaporated to dryness and the residue is treated with sodium hydroxide. A yellow solid is obtained which is filtered off, washed with water and dried.

The base thus obtained is recrystallised from methanol. 11 g of N-(1,3-dimethyl-2-oxo-5-benzimidazolylidene)-N'-amidino-hydrazine are thus obtained.

Melting point = 238° C.

EXAMPLE 12

N-(1,3-Dimethyl-2-Oxo-5-Benzimidazolylidene)-N'-Imidazolino-Hydrazine

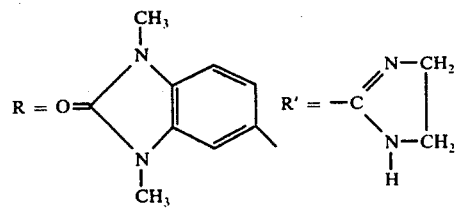

Formula I 15.5 g (0.08 mol) of 5-carboxaldehyde-1,3-dimethyl-benzimidazolone and 14.6 g (0.08 mol) of imidazolino-hydrazine hydrobromide are added to 300 cm³ of 50% strength ethanol. This mixture is heated under reflux for 7 hours after which it is evaporated to dryness and treated with sodium hydroxide. A yellow solid is obtained, which is filtered off, washed with water and dried.

The base thus obtained is washed with hot methanol to give 13.5 g of N-(1,3-dimethyl-2-oxo-5-benzimidazolylidene N'-imidazolino-hydrazine.

Melting point = 275° C.

EXAMPLE 13

N-(2-Chloro-3-Pyridylidene)-N'-Amidino-Hydrazine

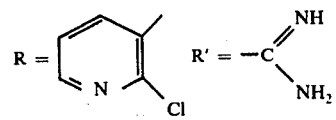

Formula I

A mixture of 13.5 of 2-chloro-nicotinaldehyde and 12.6 g of neutral aminoguanidine sulphate in 200 cm³ of ethanol and 50 cm³ of water is heated under reflux for 4 hours.

The reaction mixture is then concentrated in vacuo and thereafter rendered alkaline, in the cold, with concentrated ammonia, whilst stirring. The crystals obtained are filtered off, washed with water and dried.

12.1 g of N-(2-chloro-3-pyridylidene)-N'-amidinohydrazine are thus obtained in the form of white crystals.

Melting point = 201°-202° C.

EXAMPLE 14

6-Methoxy-1,3-Dimethyl-Benzimidazolone-5-Carboxaldehyde 14.7 g. (0.16 mole) of phosphorus oxychloride are added slowly to 12.5 cm³ of dimethylformamide. To the complex thus formed is added 28 g. (0.145 mole) of 5-methoxy-1,3-dimethylimidazolone in solution in 75 cm³ of methylene chloride. The reaction mixture is heated to 100° C for three hours, cooled and hydrolysed by adding ice. The product which precipitates is filtered off and washed with water and hot methanol. 22.5 g. of 6-Methoxy-1,3-dimethyl-benzimidazolone-5-carboxaldehyde, m.p. 240°-242° C. are obtained.

EXAMPLE 15

N-(6-Methoxy-1,3-Dimethyl-2-Oxo-5-Benzimidazolylidene)-N'-Amidino Hydrazine

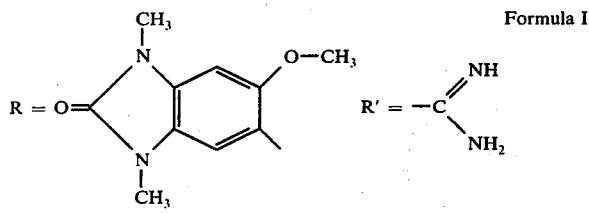

Formula I 17.4 g of 6-methoxy-1,3-dimethylbenzimidazolone-5-carboxaldehyde and 10.4 g of amidino hydrazine sulphate are added to a mixture of 500 cm³ of dioxane and 100 cm³ of water. The mixture is heated under reflux for 8 hours. The product which has precipitated is filtered off and made alkaline in the cold with concentrated ammonia solution. The base precipitates. It is separated and recrystallised from a mixture of methanol and isopropanol (50:50). 10.5 g of N-(6-methoxy-1,3-dimethyl-2-oxo-5-benzimidazolylidene)-N'-amidinohydrazine, m.p. 260° C., are obtained.

EXAMPLE 16

N-(6-Methyl-1,3-Dimethyl-2-Oxo-5-Benzimidazolylidene)-N'-Amidino Hydrazine Neutral Sulphate

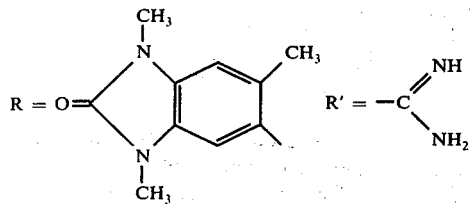

Formula I 19.6 g. of 6-Methyl-1,3-dimethylbenzimidazolone-5-carboxaldehyde and 12.7 g of amino guanidine sulphate are added to a mixture of 200 cm³ of methanol and 100 cm³ of water. The mixture is heated under reflux for 7 hours. The product which has precipitated is filtered off and washed with methanol. 24 g of the neutral sulphate of N-(6-methyl-1,3-dimethyl-2-oxo-5-benzimidazolylidene)-N'-amidino hydrazine are obtained m.p. 315° C.

EXAMPLE 17

N-[Methyl-o-(Prop-2-Ynoxy)-Benzylidine]-N'-Amidino Hydrazine

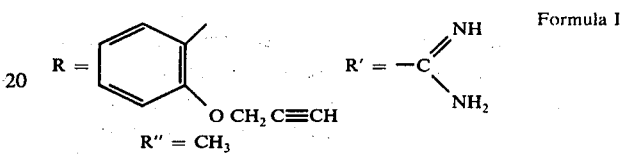

Formula I

A mixture of 0.1 mole of o-(prop-2-ynoxy)-acetophenone, 0.05 mole of amino guanidine neutral sulphate, and 80 cm³ of ethylene glycol is heated at 130° C., for 6 hours. The mixture is then diluted by adding 300 cm³ of water and extracted with ether. The aqueous phase is made alkaline by addition of sodium hydroxide and extracted with chloroform. The chloroform phase is separated, dried over anhydrous magnesium sulphate, and evaporated in vacuo.

The residue thus obtained (12 g) is taken up in 60 cm³ of ethyl acetate, and a solution of 5.4 g of oxalic acid in 60 cm³ of ethyl acetate is added. The mixture is allowed to stand for 6 hours. The precipitate is filtered off, washed with ethyl acetate, dried, and recrystallised from isopropanol. 5.8 g of the expected product, m.p. 138° C., are obtained.

The anti-hypertensive activity of the compounds according to the invention is shown by the pharmacological experiments which follow.

METHOD

Male rats aged 16 to 20 weeks and exhibiting a spontaneous genetically transmissible hypertension are placed in a heated box at 38° C. The arterial pressure is measured by a "Narco Bio System" sphygmomanometer. A sleeve is placed over the base of the tail and a detector records the pulse downstream from the sleeve. The sleeve is then inflated until the pulse is stopped, thus indicating the systolic pressure. The rate of heartbeat is also recorded.

The products to be studied are converted to a suspension by means of "Tween 80" and administered intraperitoneally in a volume of 1 cm³ per 100 grams of body weight.

The measurements are repeated at regular intervals.

The Table which follows shows the percentage variation and the mean deviation of the systolic arterial pressure and of the rate of heartbeat, 30 to 60 minutes after treatment.

| Ex. | Doses mg/kg given intra- peritoneally | Arterial pressure | | Rate of heartbeat | |
|---|---|---|---|---|---|
| | | T + 30 mins | T + 60 mins | T + 30 mins | T + 60 mins |
| 1 | 40 | −52 ± 3.4 | − 56 ± 4.3 | − 19 ± 2.1 | − 17 ± 3.2 |
| 2 | 20 | − 49 ± 5.0 | − 48 ± 1.8 | − ± 5.0 | − 12 ± 7.6 |
| 3 | 10 | − 26 ± 5.8 | − 11 ± 1.2 | − 2 ± 3.1 | − 1 ± 1.1 |
| 4 | 40 | − 44 ± 8.2 | − 30 ± 5.2 | − 20 ± 4.3 | − 13 ± 1.6 |
| 5 | 40 | − 34 ± 4.1 | − 22 ± 3.0 | − 7 ± 5.4 | − 9 ± 3.4 |
| 6 | 10 | − 30 ± 6.4 | − 17 ± 4.0 | − 3 ± 2.1 | − 3 ± 3.1 |
| 7 | 40 | − 29 ± 4.5 | − 15 ± 1.8 | − 9 ± 7.8 | − 1 ± 4.5 |
| 8 | 20 | − 23 ± 1.3 | − 22 ± 2.8 | − 6 ± 1.1 | − 10 ± 4.3 |
| 9 | 10 | − 28 ± 5.4 | − 10 ± 4.5 | − 7 ± 2.3 | − 5 ± 2.7 |
| 10 | 10 | − 28 ± 5.3 | − 20 ± 4.0 | − 4 ± 3.6 | − 2 ± 2.9 |
| 11 | 40 | − 38 ± 4.8 | − 28 ± 4.4 | − 2 ± 5.8 | + 8 ± 3.8 |
| 12 | 40 | −39 ± 7.4 | − 12 ± 3.8 | − 12 ± 3.8 | − 4 ± 3.7 |
| 13 | 20 | − 29 ± 4.2 | − 18 ± 4.1 | − 5 ± 2.2 | − 3 ± 1.3 |
| 15 | 20 | − 42 ± 7.0 | − 38 ± 4.26 | − 12 ± 8.97 | − 13 ± 6.34 |
| 16 | 40 | − 49 ± 4.37 | − 49 ± 3.75 | − 21 ± 4.63 | − 17 ± 6.68 |
| 17 | 20 | − 29 ± 5.31 | − 30 ± 6.16 | − 14 ± 3.56 | − 10± 3.04 |
| Dihydra- lazine | 1.25 | − 35 ± 5.21 | − 34 ± 8.33 | + 37 ± 9.61 | + 21 ± 5.83 |

The animals show normal behaviour.

The compounds described show an anti-hypertensive activity which is noteworthy in that it does not cause sedation or tachycardia, which distinguishes these products from currently used therapeutic agents. They have low toxicity, the lethal doses ($LD_{50}$) following intraperitoneal administration in the rat, are between 100 and 500 mg/kg. The active doses in this animal are between 20 and 40 mg./kg. following oral administration.

The compounds of Examples 1 to 13 and 15 to 17 can be used in hypertension therapy, e.g. in the form of pills or capsules containing 25 and 50 mg each of active principle, in a daily dose of 50 to 150 mg for an adult.

We claim:

1. A hydrazine derivative of the formula:

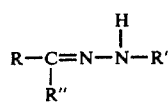

in which R is the radical of formula:

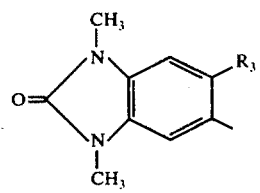

wherein $R_3$ is hydrogen, methyl or methoxy, R' is a radical of formula:

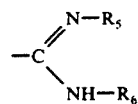

in which $R_5$ and $R_6$ are each hydrogen and R" is hydrogen and the pharmaceutically acceptable addition salts with non-toxic acids of said hydrazine derivative.

2. A hydrazine derivative according to claim 1 which is N-(1,3-dimethyl-2-oxo-5-benzimidazolylidene)-N'-amidino-hydrazine and its pharmaceutically acceptable non-toxic acid addition salts.

3. A hydrazine derivative according to claim 1 which is N-(6-methyl-1,3-dimethyl-2-oxo-5-benzimidazolylidene)-N'-amidino hydrazine and its pharmaceutically acceptable non-toxic acid addition salts.

4. A hydrazine derivative according to claim 1 which is N-(6-methyl-1,3-dimethyl-2-oxo-5-benzimidazolylidene)-N'-amidino hydrazine neutral sulphate and its pharmaceutically acceptable non-toxic acid addition salts.

5. An anti-hypertensive composition comprising, in association with a compatible pharmaceutical carrier, an effective amount of at least one compound as claimed in claim 1.

6. A composition according to claim 5 in the form of a pill or capsule containing 25 to 50 mg. of active compound.

7. A hydrazine derivative of the formula:

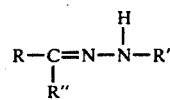

in which R is the radical of formula:

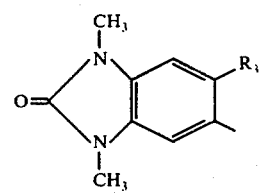

wherein $R_3$ is hydrogen, methyl or methoxy, R' is an imidazolinyl radical of formula:

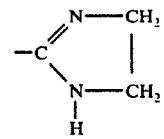

R" is hydrogen, and the pharmaceutically acceptable addition salts with non-toxic acids of said hydrazine derivative.

8. A hydrazine derivative according to claim 7 which is N-(1,3-dimethyl-2-oxo-5-benzimidazolylidene)-N'-imidazolino-hydrazine and its pharmaceutically acceptable non-toxic acid addition salts.

* * * * *